United States Patent
Van Baelen et al.

(10) Patent No.: US 9,042,996 B2
(45) Date of Patent: May 26, 2015

(54) WIRELESS COMMUNICATIONS IN MEDICAL DEVICES

(75) Inventors: Erika J. Van Baelen, Heverlee (BE); Koen Van Den Heuvel, Hove (BE); Werner Meskens, Obwijk (BE); Adam Schindhelm, Mechelen (BE); Christopher J. Long, Centennial, CO (US)

(73) Assignee: Cochlear Limited, Macquarie University, NSW (AU)

( * ) Notice: Subject to any disclaimer, the term of this patent is extended or adjusted under 35 U.S.C. 154(b) by 757 days.

(21) Appl. No.: 13/045,320

(22) Filed: Mar. 10, 2011

(65) Prior Publication Data

US 2012/0232616 A1    Sep. 13, 2012

(51) Int. Cl.
  *A61N 1/36*  (2006.01)
  *A61F 11/04* (2006.01)
  *A61N 1/372* (2006.01)
  *H04R 25/00* (2006.01)

(52) U.S. Cl.
  CPC ........ *A61N 1/36032* (2013.01); *A61N 1/37217* (2013.01); *A61N 1/3727* (2013.01); *H04R 25/552* (2013.01); *H04R 25/554* (2013.01); *H04R 25/558* (2013.01)

(58) Field of Classification Search
  CPC . A61N 1/3727; A61N 1/36032; H04R 25/552
  USPC ............................................... 607/30, 57, 60
  See application file for complete search history.

(56) References Cited

U.S. PATENT DOCUMENTS

| | | | |
|---|---|---|---|
| 4,918,736 A | 4/1990 | Bordewijk | |
| 6,978,181 B1 * | 12/2005 | Snell | ............. 607/60 |
| 7,580,534 B2 | 8/2009 | Fischer | |
| 2001/0051766 A1 | 12/2001 | Gazdzinski | |
| 2005/0089001 A1 | 4/2005 | Nishikawa | |
| 2007/0147641 A1 | 6/2007 | Platz | |
| 2008/0049945 A1 | 2/2008 | Haenggi et al. | |
| 2008/0253593 A1 | 10/2008 | Bramslow et al. | |
| 2009/0030484 A1 * | 1/2009 | Chambers | ......... 607/57 |
| 2009/0216296 A1 * | 8/2009 | Meskens | ............ 607/57 |
| 2010/0181844 A1 | 7/2010 | Karalis et al. | |

FOREIGN PATENT DOCUMENTS

| | | |
|---|---|---|
| DE | 20114461 | 10/2001 |
| EP | 1250026 | 10/2002 |
| EP | 2026406 | 2/2009 |
| WO | 03/101536 | 12/2003 |
| WO | 2004/012477 | 2/2004 |
| WO | 2004/034738 | 4/2004 |
| WO | 2006/122836 | 11/2006 |

OTHER PUBLICATIONS

Zarlink Semiconductor, Inc., http://www.zarlink.com/zarlink/zl70101-product-preview-apr2007.pdf, (2007).

(Continued)

*Primary Examiner* — Mark W Bockelman

(57) ABSTRACT

A medical device, comprising first and second components coupled via a first wireless link; and a third component coupled to the first device via a second wireless link. The device implements a communication scheme in which transmissions via the second wireless link occur during a time period that is interleaved between periods including transmissions via the first link.

25 Claims, 7 Drawing Sheets

(56) References Cited

OTHER PUBLICATIONS

International Search Report and Written Opinion for International Application No. PCT/IB2012/051130 mailed Oct. 25, 2012 (18 pages).

Gu et al., "Radio Triggered Wake-Up for Wireless Sensor Networks", Department of Computer Science, University of Virginia, Real Time Systems, Springer, vol. (29) No. 2-3, ISSN: 0922-6443, Mar. 2005, pp. 157-182 (14 pages).

Van der Doom et al., "A Prototype low-cost wakeup radio for the 868 MHz band" Int. J. Sensor Networks, vol. 5, No. 1, 2009, pp. 22-32 (11 pages).

* cited by examiner

BILATERAL SYSTEM
100

102L    102R

102L

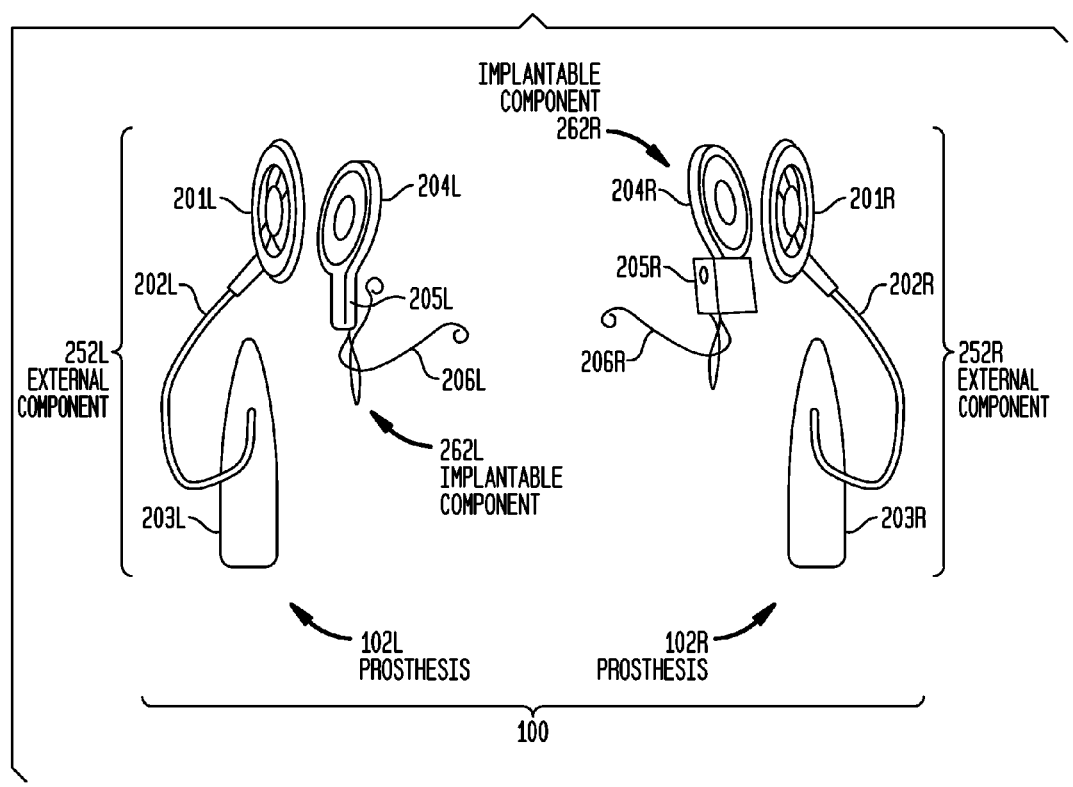

WIRELESS COMMUNICATIONS IN MEDICAL DEVICES

BACKGROUND

1. Field of the Invention

The present invention generally relates to medical devices, and more particularly, to wireless communications in medical devices.

2. Related Art

Medical devices have provided a wide range of therapeutic benefits to patients (commonly referred to as recipient's) over recent decades. One type of medical device that has provided substantial benefits to recipient's are hearing prostheses. Hearing prostheses process ambient sound to supplement or provide hearing ability to a hearing impaired patient. Hearing prostheses include, for example, hearing aids, cochlear implants, middle ear stimulators, bone conduction devices, brain stem implants, electro-acoustic devices and other devices providing acoustic, mechanical and/or electrical stimulation.

One specific hearing prosthesis is a bilateral device or system that includes two hearing prostheses, one positioned adjacent each ear of the recipient. In a bilateral system, each of the prostheses provide stimulation to enhance a recipient's perception of sound. Bilateral systems also help eliminate the head shadow effect by essentially enabling the recipient to selectively listen to sound received by which ever one of the prosthesis is positioned so as to experience a better signal to noise ratio. Additionally, inter aural time delays and level differences provide cues as to the location of the sound source and may assist in separating desired sounds from background noise.

SUMMARY

In accordance with embodiments of the present invention, an implantable medical device is provided. The device comprises: a first implantable component; and a first external component coupled to the first implantable component via a first wireless link, wherein the first external component is adapted to communicate with a second external component via a second wireless link, and wherein the device implements a communication scheme in which the first and second wireless links only operate during different sets of time periods.

In accordance with other embodiments of the present invention, a medical device is provided. The device comprises: first and second components coupled via a first wireless link; and a third component coupled to the first component via a second wireless link, wherein the device implements a communication scheme in which transmissions via the second wireless link occur during time periods that are interleaved between periods including transmissions via the first link.

In accordance with still other embodiments of the present invention, a wireless communication method in a medical device, the device including a first implantable component, and first and second external components, wherein the first external component is configured to communicate with the first implantable component via a first wireless link and to communicate with the second external component via a second wireless link is provided. The method comprises: operating the first wireless link during a first set of time periods; operating the second wireless link during a second set of time periods; and interleaving the first and second sets of time periods.

In accordance with other embodiments of the present invention, a medical device is provided. The device comprises: first and second components coupled via a first wireless link operable during; and a third component coupled to the first component via a second wireless link; and means for interleaving the operation of the first and second wireless links such that the first wireless link is operable during only during a first set of time periods and wherein the second wireless link is operable only during a second set of time periods.

BRIEF DESCRIPTION OF THE DRAWINGS

Illustrative embodiments of the present invention will now be described with reference to the accompanying figures, in which:

FIG. 2 is a schematic view of the components of the bilateral system of FIG. 1A;

DETAILED DESCRIPTION

Embodiments of the present invention will be described with reference to a particular illustrative medical device, namely a bilateral cochlear implant system. However, it would be appreciated that embodiments of the present invention may be used in any medical device or system having multiple wireless communication links. For example, embodiments of the present invention may be used in other hearing prostheses such as hearing aids, middle or inner ear direct stimulation systems, bone conduction devices, cochlear implants, brain stem and other neural stimulators, or hybrid electrical and acoustic systems. Accordingly, it would be appreciated that the specific implementations described below are merely illustrative and do not limit the scope of the present invention.

Figure 1A:
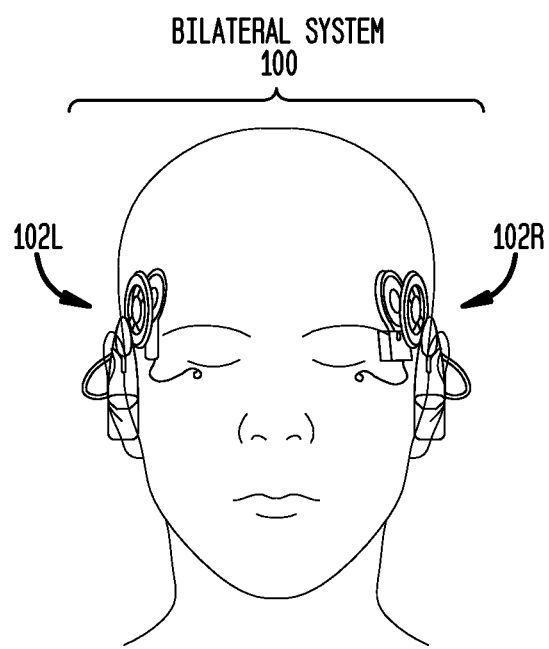
FIG. 1A is a schematic view of a bilateral cochlear implant system in which embodiments of the present invention may be advantageously implemented.
Figure 1B:
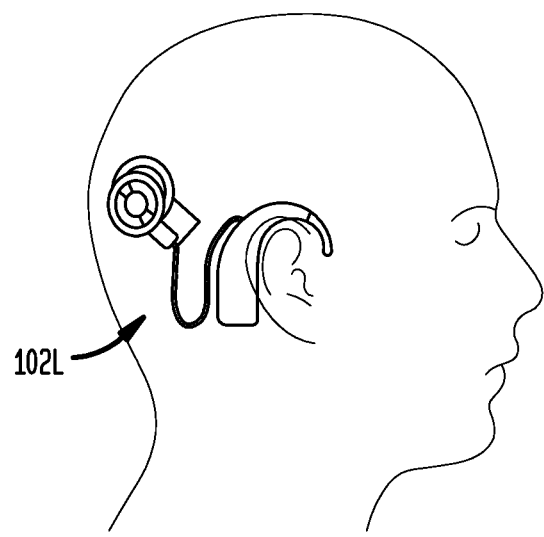
FIG. 1B is a side view of a recipient including the bilateral system of FIG. 1A.

FIGS. 1A and 1B are schematic drawings of a recipient wearing a left cochlear prosthesis 102L and a right cochlear prosthesis 102R, collectively referred to herein as a bilateral cochlear implant system 100. FIG. 2 is a schematic view of bilateral system of FIGS. 1A and 1B. As shown in FIG. 2, prosthesis 102L includes of an external component 252L comprising a sound processor 203L electrically connected to an external coil 201L via cable 202L. Prosthesis 102L also includes implantable component 262L implanted in the recipient. Implantable component 262L includes an internal coil 204L, stimulator unit 205L and an electrode array 206L implanted in the cochlea. In operation, a sound received by prosthesis 102L is converted to an encoded data signal by processor 203L, and is electromagnetically transmitted from external coil 201L to internal coil 204L via magnetic inductive RF link. This link, referred to herein as Closely Coupled Link (CCL), is also used to transmit power from external component 252L to implantable component 262L.

In the implementation of FIG. 2, prosthesis 102R is substantially the same as prosthesis 102L. In particular, prosthesis 102R includes an external component 252R comprising sound processor 203R, cable 202R and external coil 201R. Prosthesis 102R also includes implantable component 262R comprising internal coil 204R, stimulator 205R, and electrode array 206R.

Figure 3:
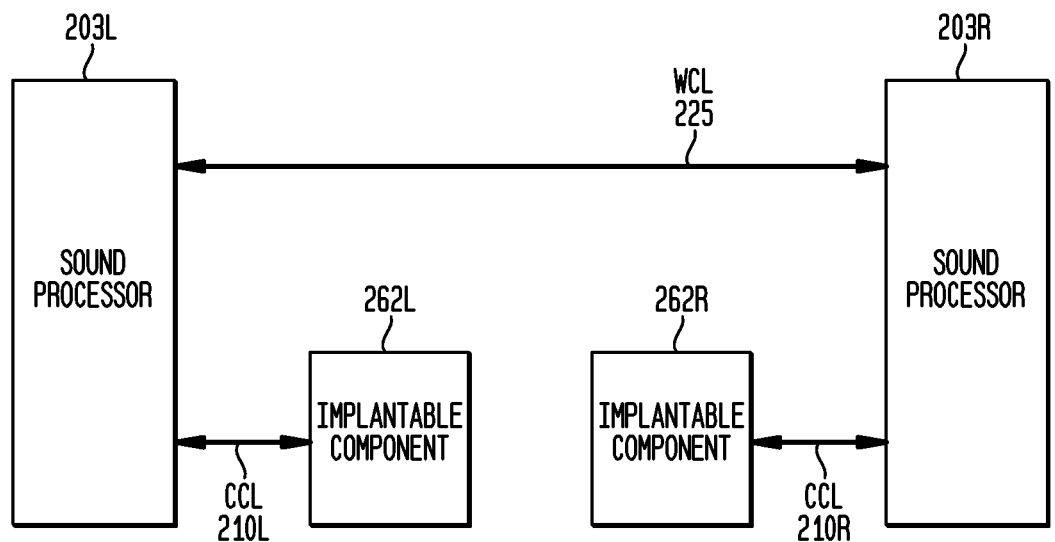
FIG. 3 is a functional block diagram of selected components of the bilateral system of FIG. 1A.

FIG. 3 is a schematic diagram that functionally illustrates selected components of bilateral system 100, as well as the communication links implemented therein. As shown, system 100 comprises sound processors 203. Sound processor 203L communicates with an implantable component 262L via a CCL 210L, while sound processor 203R communicates with implantable component 262R via CCL 210R. CCLs 210 are magnetic induction (MI) links, but, in alternative embodiments, links 210 may be of any wireless link now know or later developed. In the exemplary arrangement of FIG. 3, CCLs 210 generally operate (e.g., purposefully transmit data) at a frequency in the range of about 5 to 50 MHz.

As shown in FIG. 3 and as noted above, sound processors 203 also communicate via a separate wireless communications link (WCL) 225. In the exemplary implementation of FIG. 3, WCL 225 is a magnetic inductive (MI) link operating approximately between 2 to 15 MHz. In a specific arrangement of a bilateral system, MI link 225 may be around 5 or around 13 MHz.

As noted, a bilateral system includes multiple wireless links for various uses. Embodiments of the present invention are generally directed to controlling the wireless links within a bilateral system, such as system 100, so as eliminate or substantially reduce such interference. Specifically, with reference to FIGS. 2 and 3, system 100 implements a communication scheme, such as a time division or synchronized communication scheme, that allows for operation of WCL 225 without interference from other wireless links, such as CCLs 210. In the scheme of embodiments of the present invention, transmissions via one or both of CCLs 210 occur in a first set of time period, while transmissions via WCL 225 occur in a second set of time periods. The first and second sets of time periods are then interleaved during operation so that the CCL transmissions and WCL transmissions do not occur at the same time.

In a typical bilateral system, each prosthesis operates, at least partially, independent from the other prosthesis and, as such, each prosthesis includes one or more of its own clock generators. As is well known, a clock generator produces a clock signal that is used by the circuits and other electronic components in the prosthesis. Specifically, data processing operations, wireless communications, etc., are tied to the clock signal. In an ideal situation, the clocks of the bilateral prosthesis are synchronized with one another, so that all operations in the two prostheses are performed at substantially the same time. However, in practice, the clock of one system does not run at the exact right speed compared to the clock of the bilateral system. That is, after some time the clock "drifts apart" from the other clock. These timing and/or phase differences introduce losses of phase and temporal details upon the delivery of sound information, and may adversely affect a recipient's ability to spatially locate the source of incoming sounds, and in general reduces the advantages of bilateral system 100. Embodiments of the present invention have the advantages of allowing for the exchange of timing information between the bilateral implants to address the above timing issues via WCL 225. However, it would be appreciated that WCL 225 may also be used for other purposes, such as the exchange of data to improve localization and beamforming, exchange of user settings or processing strategies, gain management, noise reduction, environment classification, etc.

The independent operation of the prostheses of FIG. 3, and the close proximity to one another may detrimentally affect the operation of the prosthesis in such a way that the hearing benefit for the recipient is reduced. For example, due to the relatively high signal levels required for power transfer, a CCL operating on a first side of a recipient's head can produce artifacts in the telemetry signals from the opposite side. In this case, the magnetic induction receiver may become saturated, due to the high power levels of CCL 210, resulting in the loss of data. Additionally, there is a potential for interference between the CCL and the WCL, even where they do not operate at the same frequencies, and CCL operation may lead to saturation of the WCL receiver, due to out of band interference. For example, CCL 210L is operating on the recipient's left side, and telemetry data is to be sent from implant 262R to speech processor 203R (recipient's right side), the power levels of CCL 210 will likely interfere with the telemetry transmission between 262R and 203R. This interference reduces the accuracy of the reception of the data by sound processor 203R, and increases the signal to noise ratio. This interference may also affect the telemetry data path. Additionally, CCL 210L and CCL 210R could interfere with WLC 225 if operated at the same time. By implementing the scheme of embodiments of the present invention, these interference problems may at least partially be addressed because WCL 225 does not operate at the same time as CCLs 210.

Figure 4:
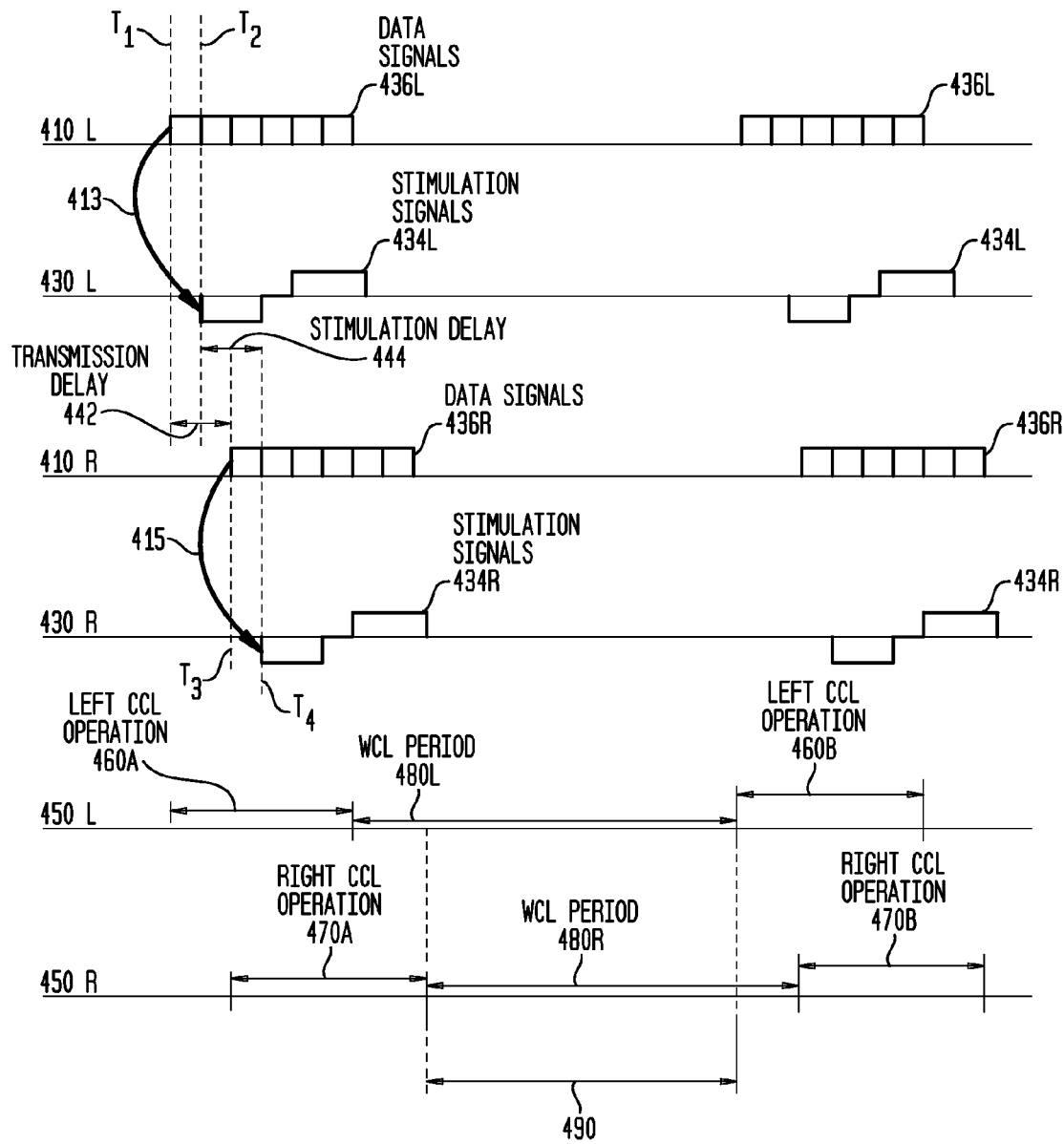
FIG. 4 is a timing diagram illustrating timing differences that may occur within a bilateral system.

FIG. 4 contains six graphs illustrating various aspects of a scheme in accordance with embodiments of the present invention. For ease of reference, FIG. 4 will be described with respect to system 100 of FIG. 3, including left and right closely coupled links (CCLs), and a wireless communication link (WCL) between the two prostheses. Graphs 410 illustrate the relative timings between transmission of data signals 436 in the right and left CCLs 210, while graphs 430 illustrate the relative timing differences between stimulation signals 434L generated based on the data signals received via the CCLs.

As shown in graph 410L, CCL 210L transmits its first data at time $T_1$, and the first stimulation pulse generated based on this data begins at $T_2$. This is shown by arrow 413. However, as shown by graph 410R, there is a time difference between the transmission of data via CCLs 210. Specifically, data transmission via CCL 210R does not begin until time $T_3$, while stimulation based thereon does not begin until $T_4$, illustrated by arrow 415. Accordingly, there is a time difference 442 between the transmission of data via link 210L at $T_1$ and the transmission of data via link 210R at $T_3$, and a corresponding time difference 444 between the commencement of stimulation at $T_2$ and $T_4$.

In embodiments of the present invention, the timing of stimulation pulses is based on the timing of data received via the CCL. FIG. 4 illustrates a direct relationship, but other, more indirect relationships are possible. Due to the dependence of the stimulation signal timing on the data signal timing, the differences in data timing affect how the recipient will perceive sound. As such, if a delay is introduced between data received via CCL 210R, with respect to CCL 210L, the recipient may not be able to properly perceive a desired sound.

As noted above, in the scheme of embodiments of the present invention, a first set of time periods are used for CCL operation/transmission, while another set of time periods are used for WCL operation/transmission. Graph 450L illustrates periods 460 allocated by the system for CCL 210L transmission, and a WCL time period 480L there between. Similarly, graph 450R illustrates periods 470 allocated by the system for CCL 210R transmission, and a WCL time period 480R there between. As described in further detail below, the system operates the links so as to provide the two types of time periods.

As shown, period 470A overlaps with WCL period 480L. Similarly, period 460B overlaps with WCL period 480R. As such, the effective window for WCL transmission is shorter, shown as window 490. As such, graphs 450 make it clear that, because the timings of the CCL transmissions do not occur at the same time, the time period for WCL transmission is less than if the timings were aligned.

Figure 5:
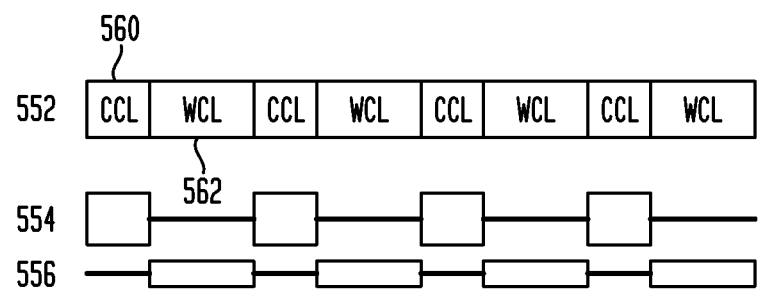
FIG. 5 is a timing diagram illustrating wireless communications in accordance with embodiments of the present invention.

FIG. 5 is a schematic schematically illustrates the timing of communications in a scheme in accordance with embodiments of the present invention in which one set of time periods is used for CCL transmission, and a second set of time periods is used for WCL transmission. More specifically, graph 552 illustrates that there are two alternating time periods, shown as CCL period 560 and WCL period 562. As shown by graphs 550 and 554, CCLs 210 (FIG. 3) operate during period 560, while WCL 225 (FIG. 3) operates during WCL period 562.

As would be appreciated, FIG. 5 illustrates embodiments in which there are generally two different alternating time periods, one period for CCL transmission, and one period for WCL transmission. It would be appreciated that the use of two time periods is merely illustrative and additional time periods may be used in other embodiments of the present invention. For example, a system may include additional wireless links that are assigned their own time periods.

Figure 6:
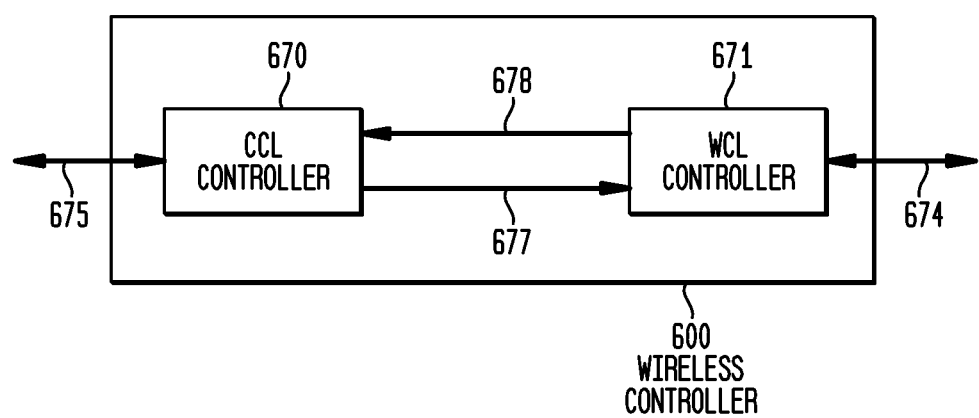
FIG. 6 is a block diagram illustrating exemplary control systems implemented in embodiments of the present invention.

FIG. 6 is a functional block diagram of elements of a prosthesis, that may implement the scheme of embodiments of the present invention. In the illustrative embodiment of FIG. 6, a wireless controller 600 is provided. Wireless controller 600 comprises a CCL controller 670 and a WCL controller 671. CCL controller 670 controls a corresponding physical system (e.g. transmitter, coil) via signal 675, while WCL controller 671 controls a corresponding physical system (e.g. antenna, transceiver) via signal 674. Controllers 670, 671, may be implemented in any combination of hardware and firmware. For ease of reference, wireless controller 600 will be described as an element of prosthesis 102L of FIGS. 2 and 3. As such, in this illustrative embodiment, CCL controller 670 operates CCL 210L, while WCL controller 671 operates WCL 225. It would be appreciated that wireless controller 600 may be implemented in any medical device.

In operation, each controller 670, 671 are informed about the status of the other controller through suitable notifications or interrupt signals. In one example, when CCL 210L is operable to transmit power/data, CCL controller 670 sends a signal 677 to WCL controller 671 indicating that CCL 210L is operational. Signal 677 may be, for example, a discrete data signal that causes WCL controller 671 to cease and/or disable WCL 225, or continuous "busy" signal 677. After the time period for CCL transmission ends, CCL controller 670 may send another signal 677 to WCL controller 671 indicating that the CCL transmission has ended and WCL transmission may commence. Alternatively, the continuous "busy" signal 677 may be removed and WCL controller 671 may commence transmission via WCL 225. CCL controller 670 tracks when the time period for WCL transmission is to end and sends another signal 677 causing WCL controller 671 to cease and/or disable WCL 225. In certain embodiments of the present invention, WCL controller 671 may send other signals 678 to CCL controller 670.

It would be appreciated that the use of a CCL controller and WCL controller, as detailed above with reference to FIG. 6, is merely illustrative and does not limit embodiments of the present invention. Various combinations of hardware and software may used in embodiments of the present invention to provide the scheme in which certain wireless links are operated during different time periods.

As previously noted, embodiments of the present invention may be implemented in a bilateral system, such as system 100, that includes two prostheses 102 positioned on opposing sides of a recipient's head. As noted above, in certain such embodiments, each prosthesis 102 includes an individual clock generator, and differences in timing and phases cause communication problems or perception problems. For example, in a scheme of embodiments of the present invention, if the CCL transmissions do not begin or end at substantially the same times, the transmission on one side of the head may start or end within the WCL transmission period on the other side of the head, thereby causing interference with the WCL. Accordingly, in certain embodiments of the present invention, the scheme may be improved by synchronizing or coordinating when wireless transmissions within the begin and end. This synchronization may be accomplished through the exchange of timing information between sound processors 203 of system 100. One such approach is to exchange data between the left and right side CCL controllers using WCL 225. Upon the exchange of data via the WCL, a trigger signal is sent by the WCL controller to the CCL controller.

Figure 7:
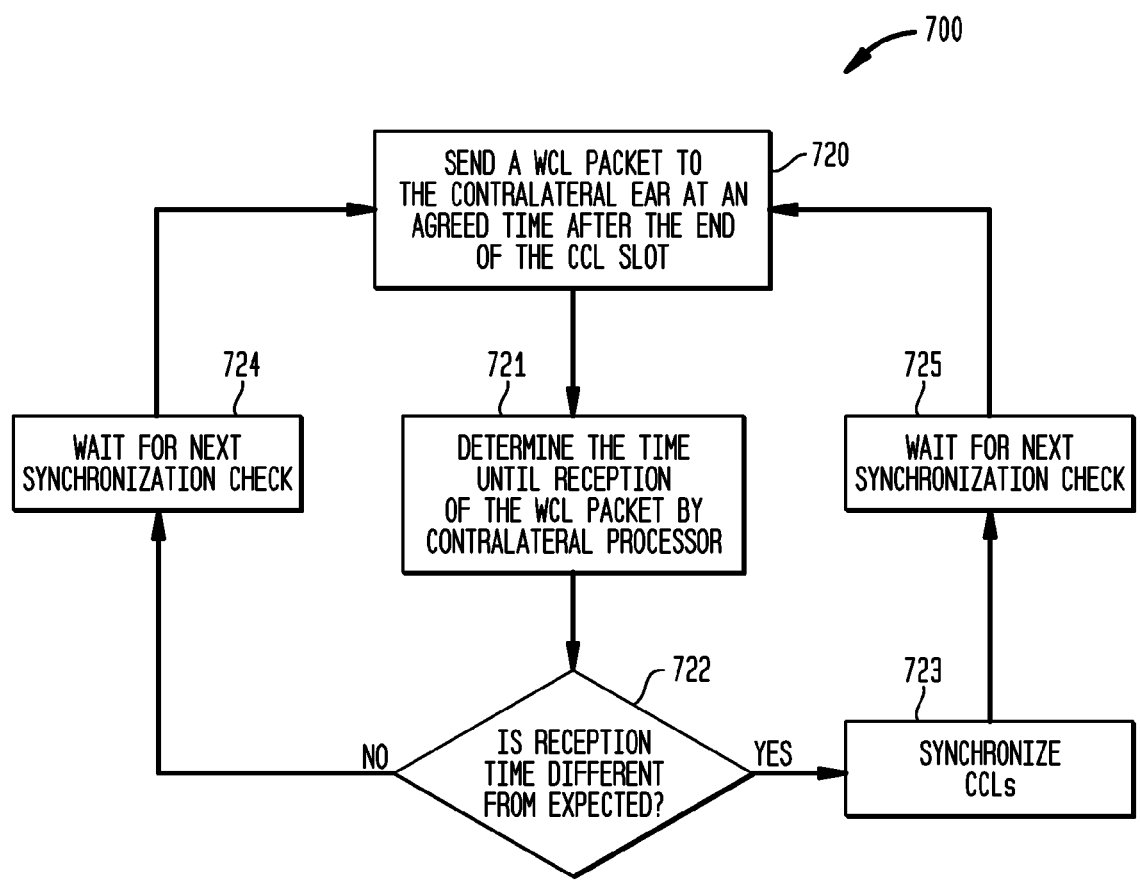
FIG. 7 is a flowchart illustrating a process for determining whether bilateral implants are synchronized, in accordance with embodiments of the present invention.

FIG. 7 is a flowchart illustrating one exemplary method 700 for determining if two bilateral prostheses, such as prostheses 102, are synchronized in accordance with embodiments of the present invention. For ease of illustration, method 700 will be described with reference to system 100 of FIG. 3.

In this specific example of FIG. 7, prosthesis 102L functions as a master, while implant 102R functions as the slave. Additionally, each sound processor 203 includes a CCL controller and a WCL controller. At block 720, the CCL controller in sound processor 203L (the master sound processor) sends a packet of data, referred to as WCL packet, to sound processor 203R via WCL link. This WCL packet is sent a predetermined time after the end of the CCL (RF) time period. The CCL time period ends once the CCL controller stops operation of the CCL.

At block 721, the time period that it took for sound processor 203R (the contralateral processor) to receive the WCL packet is determined. In certain embodiments, this time may be determined by the WCL controller in sound processor 203R, and the time is provided to sound processor 203L. In other embodiments, when sound processor 203R receives the WCL packet, a signal is sent back to sound processor 203L indicating receipt of the signal. In such embodiments, sound processor 203 uses this return signal to calculate the time.

At block 722, a decision is made as to whether time is different than is expected. If the time is not different than expected, or is within an acceptable range, prostheses 102 are substantially synchronized and method 700 proceeds to block 724. The method waits at block 724 until the system desires to confirm to check synchronization again. When the synchronization check is again desired, method will return to block 720.

Returning to block 722, if it is determined that the time difference is substantially different than expected, the system determines prostheses 102 are not synchronized. As such, method 700 proceeds to block 723 where a process is performed to substantially synchronize the CCLs. Exemplary methods for synchronizing the CCLs are described further below. After the synchronization is complete, method 700 waits at block 725 until the system desires to confirm to check synchronization again. When the synchronization check is again desired, method will return to block 720.

As noted above, if it is determined that prosthesis 102 are not synchronized, another method may be implemented to synchronize the implants. Specifically, an adjustment is made to the start time of one or both of the CCL transmissions. For example, in one variation master sound processor 203L may send a signal to processor 203R indicating that the next CCL transmission in implant 102R should occur a certain time before, or after, the planned transmission time. The delay or advance introduced is such that the next transmissions in CCL 210L and 210R will begin at substantially the same time.

It would be appreciated that other methods for synchronizing transmissions in CCLs 210 are within the scope of the present invention. For example, in one alternative process, the CCLs may be synchronized through detection of a common environmental signal by each sound processor 203. Specifically, each sound processor 203 may be configured to reset or adjust the CCL transmission timing upon receipt of a specific signal. Such signals may be a common known audio or control signal, or other signal, such as a cellular phone beacon signal. In an alternative implementation, synchronization may occur by the slave CCL controller detecting the envelope of the magnetic field generated by the master CCL controller. Additionally, both sides may contribute to the adjustment/ synchronization process. In other embodiments, the prostheses may be synchronized in response to a user input. The user input may be a voice command, a command entered via a remote control or other device, or a manipulation of a control in or on the system.

As noted above, there is a dependence of stimulation timing on the timing of data received via CCL. As such, by synchronizing CCLs 210 the delivery of electrical stimuli on each side may also be synchronized, thereby allow for timing and phase information to be better preserved.

As noted, FIG. 7 illustrates only one exemplary method for determining if prostheses 102 are synchronized with one another. In other embodiments, an implant determines itself when synchronization has been lost such, as for example, a device malfunction, etc. In such an arrangement, the device may be configured to revert to a waiting mode in which transmission does not occur until an appropriate signal has been received from the other implant.

Figure 8:
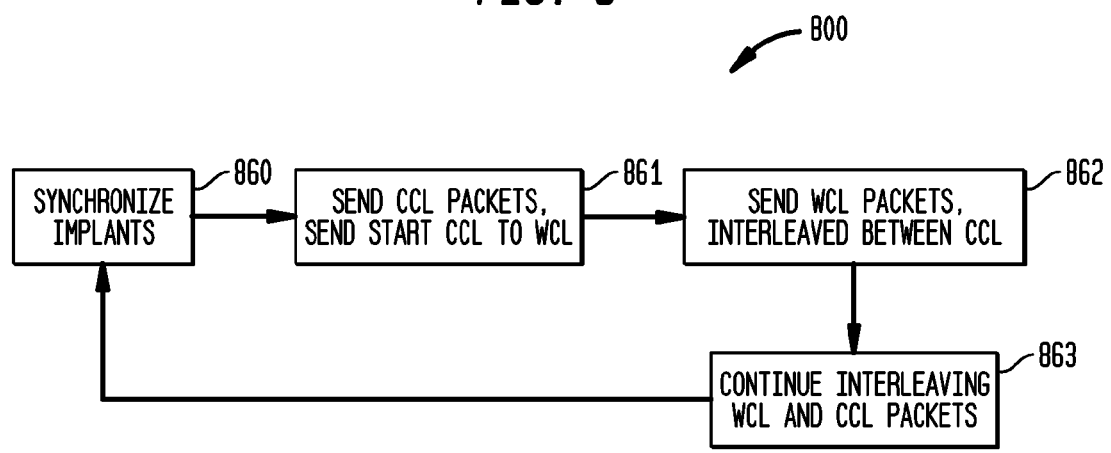
FIG. 8 is a flowchart illustrating a method for operating a bilateral system using wireless communication in accordance with embodiments of the present invention.

FIG. 8 illustrates one exemplary method 800 in accordance with embodiments of the present invention. At block 860, prostheses 102 are synchronized, using, for example, one of the approaches described above. Once synchronization is achieved, CCL power or data packets are sent at both sides using CCLs 210. As noted above with reference to FIG. 6, a signal is provided to the WCL controllers to ensure that WCL 225 does not operate while CCLs 210 are operational.

After the CCL packets are sent, WCL packets are sent at block 862. At block 863, this interleaved approach, with the WCL operating in the gaps between the CCL bursts, continues until synchronization is lost or it is desired to re-check synchronization at block 860.

Embodiments of the present invention have been primarily described herein with reference to a bilateral cochlear implant utilizing CCLs and an WCL to wirelessly communicate. However, it would be appreciated that embodiments of the present invention are not limited to devices implementing such links, but rather may be used in any medical device implemented two or more wireless links. Additionally, the links may be between any type device, or components of a device, such as between the external devices and implants, including not only stimulation devices but also power supplies, microphones and other sensors, implanted and otherwise. The wireless links may also be used to communicate with devices for controlling the hearing prosthesis, for example remote control devices and monitoring/control devices for clinicians. Additionally, embodiments include the use of time subdivisions within the each individual wireless links for use by different channels or devices.

Furthermore, embodiments of the present invention also encompass different variations in frequency channel use. For example, the CCL could use one frequency for one direction, and another for the reverse link. Some examples of suitable frequencies for the WCL are 10.7 MHz, 433 MHz, or 2.4 GHz. The WCL could, for example, use pulsed signal shapes, frequency hopping, or other known transmission coding approaches. Packet length could be fixed, or vary dynamically depending upon requirements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. All documents, patents, journal articles and other materials cited in the present application are hereby incorporated by reference.

What is claimed is:

1. An implantable medical device, comprising:
a first implantable component including wireless communication circuitry; and
first and second external component including wireless communication circuitry, wherein the wireless communication circuitry of the first external component is coupled to the wireless communication circuitry of the first implantable component via a first wireless link, wherein the wireless communication circuitry of the first external component is adapted to communicate with wireless communication circuitry of the second external component via a second wireless link, and wherein the wireless communication circuitry of the second external component is adapted to be coupled to the wireless communication circuitry of a second implantable component via a third wireless link; and
a controller configured to implement a communication scheme in which the first and second wireless links only operate during different sets of time periods and in which the first and third wireless links during the same time period.

2. The device of claim 1, wherein the second external component comprises a remote control.

3. The device of claim 1, wherein the first wireless link is operable to transmit at least one of power and data.

4. The device of claim 1, wherein the first wireless link comprises a closely coupled magnetic link.

5. The device of claim 1, wherein the first wireless link is operable only in a first series of time periods and the second wireless link is operable only in a second series of time periods, and wherein the scheme interleaves the first and second series of time periods.

6. The device of claim 1, wherein the first and second implantable components are each configured to deliver stimulation generated based on data received via the first and third wireless links, respectively.

7. The device of claim 1, wherein the controller is configured to synchronize the first and third wireless links such that the links begin transmission at substantially the same time.

8. The device of claim 7, wherein the first external component functions as a master component and the second external component functions as a slave component, and wherein the timing of the transmissions in the third wireless link are adjustable to match the timing of transmissions of the first wireless link.

9. The device of claim 7, wherein the controller is configured to synchronize the first and third wireless links in response to a specific environmental signal.

10. The device of claim 9, wherein the environmental signal is a cell phone beacon.

11. The device of claim 7, wherein the controller is configured to synchronize the first and third wireless links in response to user input.

12. The device of claim 1, wherein the first wireless link operates at a first frequency, and wherein the second wireless link operates at a second frequency that is different than the first frequency.

13. The device of claim 1, wherein the first wireless link is operable to transmit at least one of power and data.

14. A medical device, comprising:
a first external component including wireless communication circuitry;
a second implantable component including wireless communication circuitry coupled to the wireless communication circuitry of the first component via a first wireless link;
a third component including wireless communication circuitry coupled to the wireless communication circuitry of the first component via a second wireless link;
a fourth component including wireless communication circuitry coupled to the wireless communication circuitry of the third component via a third wireless link; and
a controller configured to implement a communication scheme in which transmissions via the second wireless link occur during time periods that are interleaved between periods including transmissions via the first link and to synchronize the first and third wireless links such that the links begin transmission at substantially the same time.

15. The device of claim 14, wherein the first wireless link comprises a closely coupled magnetic link.

16. The device of claim 14, wherein the second implantable component is configured to deliver stimulation generated based on data received via the first wireless link.

17. The device of claim 14, wherein the first component functions as a master component and third component functions as a slave component, and wherein the timing of the transmissions in the third wireless link are adjustable to match the timing of transmissions of the first wireless link.

18. The device of claim 14, wherein the controller is configured to synchronize the first and third wireless links in response to a specific environmental signal.

19. The device of claim 14, wherein the third component comprises a remote control.

20. A wireless communication method in a medical device, the device including first and second implantable components each including wireless communication circuitry, and first and second external components each including wireless communication circuitry, wherein the wireless communication circuitry of the first external component is configured to communicate with the wireless communication circuitry of the first implantable component via a first wireless link and to communicate with the wireless communication circuitry of the second external component via a second wireless communications link and wherein the wireless communication circuitry of the second implantable component is coupled to the wireless communication circuitry of the second external component via a third wireless link, the method comprising:
operating the first and third wireless links during a first set of time periods;
operating the second wireless link during a second set of time periods; and
interleaving the first and second sets of time periods.

21. The method of claim 20, further comprising:
synchronizing the first and third wireless links such that transmissions begin on the links at substantially the same time.

22. The method of claim 21, wherein synchronizing the first and third wireless links comprises:
adjusting the start time of the transmissions on the third wireless link to substantially match the start time of transmissions on the first wireless link.

23. A medical component device, comprising:
a first external component including wireless communication circuitry;
a second implantable component including wireless communication circuitry coupled to the wireless communication circuitry of the first component via a first wireless link;
a third component including wireless communication circuitry coupled to the wireless communication circuitry of the first component via a second wireless link;
a fourth component including wireless communication circuitry coupled to the wireless communication circuitry of the third component via a third wireless link;
means for synchronizing the first and third wireless links such that the links begin transmission at substantially the same time; and
means for interleaving the operation of the first and second wireless links such that the first wireless link is operable only during a first set of time periods and wherein the second wireless link is operable only during a second set of time periods.

24. The device of claim 23, further comprising:
means for adjusting the timing of the transmissions in the third wireless link to match the timing of transmissions of the first wireless link.

25. The device of claim 24, wherein the device comprises:
means for synchronizing the first and third wireless links in response to a specific environmental signal.

* * * * *

UNITED STATES PATENT AND TRADEMARK OFFICE
CERTIFICATE OF CORRECTION

| | |
|---|---|
| PATENT NO. | : 9,042,996 B2 |
| APPLICATION NO. | : 13/045320 |
| DATED | : May 26, 2015 |
| INVENTOR(S) | : Erika J. Van Baelen et al. |

Page 1 of 1

It is certified that error appears in the above-identified patent and that said Letters Patent is hereby corrected as shown below:

In the claims

Column 8, Line 55, after "links" insert the word --operate--

Signed and Sealed this
First Day of March, 2016

Michelle K. Lee
*Director of the United States Patent and Trademark Office*